United States Patent [19]

Kallman et al.

[11] Patent Number: 5,846,974
[45] Date of Patent: Dec. 8, 1998

[54] METHOD FOR TREATING SUBSTANCE ABUSE WITHDRAWAL

[75] Inventors: Mary J. Kallman, Greenfield; Kurt Rasmussen, Fishers, both of Ind.

[73] Assignee: Eli Lilly and Company, Indianapolis, Ind.

[21] Appl. No.: 984,206

[22] Filed: Dec. 3, 1997

Related U.S. Application Data

[62] Division of Ser. No. 695,451, Aug. 12, 1996, Pat. No. 5,732,717.

[60] Provisional application No. 60/002,341 Aug. 15, 1995.

[51] Int. Cl.$^6$ .............................................. A61K 31/505
[52] U.S. Cl. ........................ 514/269; 514/256; 514/812
[58] Field of Search ................................. 514/269, 256, 514/812

[56] References Cited

U.S. PATENT DOCUMENTS

| | | |
|---|---|---|
| 4,201,211 | 5/1980 | Chandrasekaran et al. . |
| 4,255,439 | 3/1981 | Cooper ................................ 514/813 |
| 4,292,303 | 9/1981 | Keith et al. . |
| 4,323,570 | 4/1982 | Stenzel et al. . |
| 4,382,946 | 5/1983 | Sjoerdsma ........................... 514/401 |
| 4,555,397 | 11/1985 | Bachynsky ........................... 514/813 |
| 4,575,510 | 3/1986 | Sjoerdsma . |
| 4,588,739 | 5/1986 | Glassman . |
| 4,683,231 | 7/1987 | Glassman ............................. 514/220 |
| 4,783,456 | 11/1988 | Glassman ............................. 514/214 |
| 4,788,189 | 11/1988 | Glazer . |
| 4,839,177 | 6/1989 | Colombo et al. . |
| 4,882,163 | 11/1989 | Guse et al. . |
| 4,952,410 | 8/1990 | Armah et al. . |
| 4,956,391 | 9/1990 | Sapse ................................... 514/810 |
| 5,051,426 | 9/1991 | Parnell ................................. 514/263 |
| 5,234,947 | 8/1993 | Cherksey ............................. 514/449 |
| 5,422,123 | 6/1995 | Conte et al. . |
| 5,464,633 | 11/1995 | Conte et al. . |
| 5,574,052 | 11/1996 | Rose et al. ........................... 514/343 |

OTHER PUBLICATIONS

Planitz, V. "Crossover comparsion of moxonidine and clonidine in mild to moderate hypertension," Eur J. Clin. Pharmacol., 27, 147–152 (1984).

Regunathan et al., "Effects of moxonidine, an imidazoline antihypertensive agent, on second messenger systems in rat brian," Eur. J. Pharmacol. Molecular Pharmacol., 269(2), 273–276 (1994).

Glavin et al., "Effects of the selective I–1 imidazoline receptor agonist, moxonidine, on gastric secretion and gastric mucosal injury in rats," Brit. J. Pharmacol., 114, 751–754 (1995).

Haxhiu et al., "Effect of I–1–imidazoline receptor activation on responses of hypoglossal and phrenic nerve to chemical stimulation," Ann New York Acad. Sci., 763, 445–462 (1995).

Webster et al., "Aspects of tolerability of centrally acting antihypertensive drugs," J. Cardiovasc. Pharmacol., 27 (suppl. 3), S49–S54 (1996).

Rupp et al., "Drug withdrawal and rebound hypertension," Cardiovasc. Drugs, Therap., 10 (suppl. 1), 251–262 (1996).

Scientific Information Brochure, Selective imidazoline receptor agonist for the treatment of hypertension, Beiersdorf–Lilly and Lilly Deutshland.

J. P. Ollivier et al., $I_1$–Imidazoline–Receptor Agonists in the Treatment of Hypertension: An Appraisal of Clinical Experience, *Journal of Cardiovascular Pharmacology*, 24 (Suppl. 1), S39–S48 (1994).

U.S. application No. 08/659463, McNay, filed Jun. 6, 1996.

Paul Ernsberger et al., Moxonodine: A Second–generation Central Antihypertensive Agent, *Cardiovascular Drug Reviews*, vol. 11, No. 4, 411–431 (1993).

Martin C. Michel et al., From $\alpha_2$–Adrenoceptors to Imidazoline Receptors: Putative Progress for Cardiovascular Therapy, *Journal of Cardiovascular Pharmacology*, 20 (Suppl. 4 ), S24–S30 (1992).

G. Trieb, M.D., et al., Long–term evaluation of the antihypertensive efficacy and tolerability of the orally acting imidazoline $I_1$ receptor agonist moxonidine, *European Journal of Clinical Research*, vol. 7, 227–240 (1995).

Selective Imidazoline Receptor Agonist, *Moxonidine Physiotens*, (Jun., 1996).

K. I. Pearce, Clonidine And Smoking, *The Lancet*, 810 (1986).

Alexander H. Glassman et al., Cigarette Craving, Smoking Withdrawal, and Clonidine, *Science*, vol. 226, 864–866 (1984).

Lirio S. Covey et al., A meta–analysis of double–blind placebo–controlled trials of clonidine for smoking cessation, *British Journal of Addiction*, 86, 991–998 (1991).

Alexander H. Glassman et al., Future Trends in the Pharmacological Treatment of Smoking Cessations, *Drugs*, 40(I), 1–5 (1990).

Lirio S. Covey, Ph.D. et al., New Approaches to Smoking Cessation, *Drug Therapy*, 55–58 (1990).

Margaret A. Willan, Effectiveness of Clonidine in Smoking Cessation, *The Canadian Journal of Hospital Pharmacy*, vol. 45, No. 2, 77–78 (1992).

Allan V. Prochazka, M.D. et al., Transdermal Clonidine Reduced Some Withdrawal Symptoms but Did not Increase Smoking Cessation, *Arch Intern Med.*, vol. 152, 2065–2069 (1992).

Peter Franks, M.D. et al., Randomized, Controlled Trial of Clonidine for Smoking Cessation in a Primary Care Setting, *JAMA*, vol. 262, No. 21, 3011–3013 (1989).

(List continued on next page.)

Primary Examiner—Leonard Schenkman
Attorney, Agent, or Firm—John C. Demeter; David E. Boone

[57] ABSTRACT

This invention provides a method for treating a condition resulting from the cessation or withdrawal of tobacco or nicotine, opioids, ethanol or combinations thereof comprising administering an effective amount of 4-chloro-5-(imidazoline-2-y(amino)-6-methoxy-2-methylpyrimidine.

9 Claims, No Drawings

OTHER PUBLICATIONS

William S. Bond, Psychiatric Indications for Clonidine: The Neuropharmacologic and Clinical Basis, *J. Clin. Psychopharmacol*, vol. 6, No. 2, 81–87 (1986).

Steven G. Gourlay et al., Is Clonidine an Effective Smoking Cessation Therapy?, *Drugs*, 50(2), 197–207 (1995).

Herbert D. Kleber, M.D., Clonidine and Naltrexone in the Outpatient Treatment of Heroin Withdrawal, *Am. J. Drug Alcohol Abuse*, 13 (1 & 2), 1–17 (1987).

Daniel E. Hilleman et al., Randomized, Controlled Trial of Transdermal Clonidine For Smoking Cessation, *The Annals of Pharmacotherapy*, vol. 27, 1025–1028 (1993).

Steven Gourlay et al., A placebo–controlled study of three clonidine doses for smoking cessation, *Clinical Pharmacology & Therapeutics*, vol. 55, No. 1, 64–69 (1994).

Alexander H. Glassman, M.D. et al., Heavy Smokers, Smoking Cessation, and Clonidine, *JAMA*, vol. 259, No. 19 (1988).

Hao Wei, M.D. et al., Effect of Clonidine on Cigarette Cessation and in the Alleviation of Withdrawal Symptoms, *British Journal of Addiction*, 83, 1221–1226 (1988).

Alexander H. Glassman, M.D. et al., Smoking cessation, clonidine, and vulnerability to nicotine among dependent smokers, *Clinical Pharmacology & Therapeutics*, vol. 54, No. 6, 670–679 (1993).

Richard Davison, M.D. et al., The effect of clonidine on the cessation of cigarette smoking, *Clin. Pharmacol Ther.*, vol. 44, No. 3, 265–267 (1988).

Steven A. Ornish et al., Effects of Transdermal Clonidine Treatment on Withdrawal Symptoms Assciated With Smoking Cessation, *Arch Intern Med.*, vol. 148, 2027–2031 (1988).

S. Said et al., Essais contrôlés randomisés d'aides médicamenteuses de l'arrrêt du tabac –Résultats et perspectives, *Therapie*, 49, 313–319 (1994).

José Luis Cervantes Escárcega et al., Efecto De La Terapia Transdermica Con Clonidina En Los Sintomas De Supresion Secundarios Al Cese Del Consumo De Tabaco, *Arch Inst. Cardiol Méx*, vol. 62, 435–440 (1992).

Pr. G. Lagrue, Clonidine, Dépression et Arrêt Du tabac, *Concours Med.*, 2260–2261 (1988).

Diane Moniz, PharmD, Clonidine and Cigarettes, *Hospital Therapy*, 171–172, 174 (1990).

Steven G. Gourlay et al., Antismoking products, *The Medical Journal of Australia*, vol. 153, 699–707 (1990).

METHOD FOR TREATING SUBSTANCE ABUSE WITHDRAWAL

This application is a division of application Ser. No. 08/695,451, filed on Aug. 12, 1996 U.S. Pat. No. 5,732,717, which claims the benefit of U.S. provisional application No. 60-002-341, filed Aug. 15, 1995.

FIELD OF THE INVENTION

The present invention is in the fields of pharmacology and pharmaceutical chemistry and provides a method for using 4-chloro-5-(imidazoline-2-ylamino)-6-methoxy-2-methylpyrimidine, for the treatment of smoking cessation, nicotine withdrawal, opioid withdrawal, ethanol withdrawal, and combinations thereof, and alleviation of the craving for a tobacco product, nicotine, opioids, ethanol and combinations thereof.

BACKGROUND OF THE INVENTION

It is well known that the chronic administration of nicotine, opioids, ethanol or combinations thereof results in tolerance and, eventually, dependence. The use of tobacco, opioids, and ethanol are extremely widespread in many countries, despite the well known adverse effects of their use.

Many people who regularly use tobacco products would like to quit but cannot because they are addicted to the psychoactive drug that is the dependence-producing constituent of tobacco, nicotine, Benowitz, N. Eng. J. Med., 319:20, 1318–1330 (1988).

Benowitz notes that nicotine may also contribute to various diseases, including cancer, heart disease, respiratory disease and other conditions, for which tobacco use is a risk factor, particularly heart disease. Nicotine is present in cigarettes and other tobacco products that are smoked or chewed. These tobacco products are addictive and associated with heart and lung diseases, and other serious disease states.

Vigorous campaigns against the use of tobacco have taken place, and it is now common knowledge that the cessation of tobacco use brings with it numerous unpleasant withdrawal symptoms, which include irritability, anxiety, restlessness, lack of concentration, lightheadedness, insomnia, tremor, increased hunger and weight gain, and, of course, an intense craving for tobacco.

A few pharmaceutical agents have been reported as useful to treat nicotine dependence, including clonidine, an $\alpha_2$-adrenergic agonist, and alprazolam, a benzodiazepine agonist. Receptor antagonists such as mecamylamine have also been used. A few of the benzodiazepine psychotropic drugs have been described as of some use in tobacco cessation but are not in widespread use. Some serotonin affecting drugs have been described as anti-smoking aids, particularly including buspirone, which has been described by West et al. as a promising aid to people trying to cease the use of tobacco, *Psychopharmacology* 104:91–96 (1991).

Benowitz reports that the most effective treatment thus far has been nicotine substitution therapy, using nicotine gum, or nicotine-providing transdermal patches to slowly wean individuals from their-addiction to nicotine and their use of tobacco products containing nicotine. Unfortunately, the nicotine substitution therapy involves the administration of the psychoactive constituent of tobacco. Nicotine substitution must be tapered, frequently leading to nicotine withdrawal and subsequent relapse to use of tobacco products. Nicotine replacement is generally accepted as most effective when combined with habit-modifying psychological treatment and training. There is a need for a therapy having a desirable side effect profile, to relieve nicotine withdrawal symptoms, including the long term cravings for nicotine.

The opioids are well known psychoactive drugs that, with use, induce tolerance and dependence upon the psychoactive drug being administered. Drug abuse and dependence, particularly of opioids, are viewed with concern by the world community. Withdrawal symptoms from the cessation of opioid use vary greatly in intensity depending on numerous factors including the dose of the opioid used, the degree to which the opioid effects on the CNS are continuously exerted, the duration of chronic use, and the rate at which the opioid is removed from the receptors. These withdrawal symptoms include craving, anxiety, dysphoria, yawning, perspiration, lacrimation, rhinorrhoea, restless and broken sleep, irritability, dilated pupils, aching of bones, back and muscles, piloerection, hot and cold flashes, nausea, vomiting, diarrhea, weight loss, fever, increased blood pressure, pulse and respiratory rate, twitching of muscles and kicking movements of the lower extremities.

Although oral opioids are relatively nontoxic, chronic use is associated with minor endocrine abnormalities, constipation and some sleep disturbance. Nevertheless, the life expectancy of opioid addicts is markedly reduced, due to overdose, drug-related infections, suicide and homicide.

Medical complications associated with injection of opioids include a variety of pathological changes in the CNS including degenerative changes in globus pallidus, necrosis of spinal gray matter, transverse myelitis, amblyopia, plexitis, peripheral neuropathy, Parkinsonian syndromes, intellectual impairment, personality changes, and pathological changes in muscles and peripheral nerves. Infections of skin and systemic organs are also quite common including staphylococcal pneumonitis, tuberculosis, endocarditis, septicemia, viral hepatitis, human immunodeficiency virus (HIV), malaria, tetanus and osteomyelitis.

Pharmaceutical agents used in treating opioid dependence include methadone, which is an opioid, and opioid antagonists, primarily naloxone and naltrexone. Clonidine has been shown to suppress some elements of opioid withdrawal but suffers from the side effects of hypotension and sedation, which can be quite extreme. Habit-modifying psychological treatment and training are frequently adjunctive therapy used in association with pharmaceutical agents. There is a need for a therapy having a more desirable side effect profile, to relieve opioid withdrawal symptoms.

Ethanol is probably the most frequently used depressant in most cultures and a major cause of morbidity and mortality. Repeated intake of large amounts of ethanol can affect nearly every organ system in the body, particularly the gastrointestinal tract, cardiovascular system, and the central and peripheral nervous systems. Gastrointestinal effects include gastritis, stomach ulcers, duodenal ulcers, liver cirrhosis, and pancreatitis. Further, there is an increased rate of cancer of the esophagus, stomach and other parts of the gastrointestinal tract. Cardiovascular effects include hypertension, cardiomyopathy and other myopathies, significantly elevated levels of triglycerides and low-density lipoprotein cholesterol. These cardiovascular effects contribute to a marked increase risk of heart disease. Peripheral neuropathy may be present as evidenced by muscular weakness, parathesias, and decreased peripheral sensation. Central nervous system effects include cognitive deficits, severe memory impairment degenerative changes in the cerebellum, and ethanol-induced persisting amnesiac disorder in which the ability to encode new memory is severely impaired. Generally, these effects are related to vitamin deficiencies, particularly the B vitamins.

Individuals with ethanol dependence exhibit symptoms and physical changes including dyspepsia, nausea, bloating, esophageal varices, hemorrhoids, tremor, unsteady gait, insomnia, erectile dysfunction, decreased testicular size, feminizing effects associated with reduced testosterone levels, spontaneous abortion, and fetal alcohol syndrome. Symptoms associated with ethanol cessation or withdrawal include nausea, vomiting, gastritis, hematemises, dry mouth, puffy blotchy complexion, and peripheral edema.

The generally accepted treatment of ethanol withdrawal symptoms and conditions is accomplished by administering a mild tranquilizer such as chloridiazepoxide. Typically, vitamins, particularly the B vitamins, are also administered. Optionally, magnesium sulfate and/or glucose are also administered. Nausea, vomiting and diarrhea are treated symptomatically at the discretion of the attending physician. Disulfiram may also be administered for help in maintaining abstinence. If ethanol is consumed while on disulfiram, acetaldehyde accumulates producing nausea and hypotension. There is a need for a therapy, effective in relieving symptoms and conditions resulting from ethanol withdrawal having a more desirable side effect profile.

There is a definite need in substance abuse withdrawal therapy for a pharmaceutical agent to relieve withdrawal symptoms and conditions that is not itself an addictive agent, as with nicotine and methadone; a receptor antagonist, such as naloxone and naltrexone, that induces or exacerbates withdrawal symptoms and conditions; or an enzyme inhibitor that induces or exacerbates withdrawal symptoms and conditions; and has an acceptable side effect profile.

Surprisingly, applicants have discovered that 4-chloro-5-(imidazoline-2-ylamino)-6-methoxy-2-methylpyrimidine can be useful for treating symptoms and conditions produced by cessation or withdrawal from the use of nicotine and tobacco products, opioids, or ethanol and combinations thereof.

SUMMARY OF THE INVENTION

The presently claimed invention provides a method for inhibiting one or more symptoms or a condition resulting from cessation or withdrawal from the use of tobacco, nicotine, opioids, ethanol or combinations thereof comprising administering an effective amount of 4-chloro-5-(imidazoline-2-ylamino)-6-methoxy-2-methylpyrimidine or a pharmaceutically acceptable salt thereof to a mammal in need of such treatment.

The invention also provides a method of assisting a mammal who uses tobacco, nicotine, opioids, ethanol or combinations thereof to cease or reduce such use, as well as a method of preventing a mammal who has ceased or reduced the use of tobacco, nicotine, opioids, ethanol or combinations thereof from resuming such use, comprising administering to such mammal an effective amount of 4-chloro-5-(imidazoline-2-ylamino)-6-methoxy-2-methylpyrimidine or a pharmaceutically acceptable salt thereof.

DETAILED DESCRIPTION OF THE INVENTION

Substance (nicotine, opioid and ethanol) dependence is a cluster of cognitive, behavioral and physiological symptoms demonstrating there is a continuing use of the substance despite significant substance-related problems. There is a pattern of repeated self-administration that results in tolerance, withdrawal and compulsive substance-taking behavior.

Tolerance is the need for significantly increased amounts of the substance to achieve the desired effect, or a markedly diminished effect with continued use of the same amount of the substance.

Generally, withdrawal is a behavioral change, having physiological and cognitive components, that occurs when blood or tissue concentrations of a substance decline in an individual who had maintained prolonged heavy use of the substance. After developing withdrawal symptoms, an individual is likely to take the substance to relieve or avoid those symptoms.

The compound 4-chloro-5-(imidazoline-2-ylamino)-6-methoxy-2-methylpyrimidine (moxonidine) is known and described in U.S. Pat. No. 4,323,570 which is incorporated herein by reference in its entirety.

As used herein, the term "mammal" means the Mammalia class of higher vertebrates. The term "mammal" includes, but is not limited to, a human. The term "treating" as used herein includes therapeutic and prophylaxis of the symptoms and named condition and amelioration or elimination of the conditions once it has been established.

As used herein, the term "opioid" means any natural opioid (opiate), semisynthetic and synthetic exogenous substance that binds to one or more opioid receptor subtype and produces agonist action. The three known opioid receptor subtypes include mu, kappa and delta. Examples of opioids include opium, morphine, heroin, codeine, pentazocine, buprenorphine, meperidine, butorphanol, feutanyl, nalbuphine, hydromorphone, oxycodone, oxymorphone and methadone.

As used herein, the term "withdrawal" or "cessation and withdrawal" shall refer to symptoms and conditions resulting from: diminished or discontinued administration and use of tobacco products, diminished and discontinued administration and use of nicotine, diminished or discontinued administration and use, injection or orally, of one or more opioid, diminished or discontinued administration and use of ethanol, and any combination of two or more thereof. Such nicotine, opioid, and ethanol withdrawal symptoms and conditions are characterized in the DSM-IV, *Diagnostic and Statistical Manual of Mental Disorders*, 4th Ed. (1994). The DSM-IV was prepared by the Task Force on Nomenclature and Statistics of the American Psychiatric Association, and provides clear descriptions of diagnostic categories. The skilled artisan will recognize that there are alternative nomenclatures, nosologies, and classification systems for pathologic psychological conditions and that these systems evolve with medical scientific progress.

The criteria for substance dependence set forth in DSM-IV is a pattern of substance use, leading to clinically significant impairment or distress as manifested by at least three selected from the following group, occurring at any time within the same twelve month period: (1) tolerance as defined by either (a) a need for substantially increased amounts of the substance to achieve the desired effect; or (b) substantially diminished effect with continued use of the same amount of the substance; (2) withdrawal, as demonstrated by either (a) the characteristic withdrawal syndrome for the specific substance; or (b) the same, or a closely related substance is taken to relieve or avoid withdrawal symptoms; (3) the substance is often taken in larger amounts or over a longer period then was intended; (4) there is a persistent desire or unsuccessful efforts to cut down or control substance use; (5) a great deal of time is spent in activities to obtain the substance, use the substance, or recover from its effects; (6) important social, occupational or recreational activities are given up or reduced because of substance use; and (7) the substance use is continued despite knowledge of having a persistent or recurrent physical or psychological problem that is likely to have been caused or exacerbated by the substance.

Substance dependence can be with physiological dependence; that is evidence of tolerance or withdrawal is present, or without physiological dependence, where no evidence of tolerance or withdrawal is present.

Four of the conditions include remission. These types of remission are based on the interval of time that has elapsed since the cessation of dependencies and whether there is continued presence of one or more of the symptoms included in the criteria for dependencies.

The qualifier "early full remission" is used when for at least one month, but for less than twelve months, no symptom of dependence has been met.

The qualifier "early partial remission" is used when for at least one month but less than 12 months, one or more symptoms for dependence has been met, but the full criteria for dependence has not been met.

The term "sustained full remission" is used when none of the symptoms of dependence have been met at any time during a period of twelve months or longer.

The term "sustained partial remission" is used if the symptoms for dependence have not been met for a period of twelve months or longer, however, one or more symptom for dependence has been met.

The qualifier "on agonist therapy" is used if the subject is on a prescribed agonist medication and no symptom for dependence has been met for that class of medication for at least the past month. It also applies to those being treated for dependence using a partial agonist.

The term "in a controlled environment" is used if the subject is in an environment where access to substances of abuse are restricted and no symptom for dependence has been met for at least the past month.

With substance withdrawal, the essential feature is the development of a substance-specific behavioral change, with physiology and cognitive concomitants, that is due to the cessation of, or reduction in, heavy and prolonged substance use. The substance-specific symptoms cause clinically significant distress or impairment in social, occupational or other important areas of functioning. These symptoms are not due to a general medical condition and are not better accounted for by another mental disorder. Withdrawal usually, but not necessarily, is associated with substance dependence. Individuals with withdrawal have a craving to readminister the substance to reduce these symptoms. Withdrawal develops when doses of the substance are reduced or stopped.

Therefore, the term "cessation and withdrawal" shall include, but is not limited to, the following conditions characterized in the DSM-IV: Nicotine Withdrawal; Nicotine-Related Disorder Not otherwise Specified; Nicotine Dependence, with physiological dependence; Nicotine Dependence, without physiological dependence; Nicotine Dependence, Early Full Remission; Nicotine Dependence, Early Partial Remission; Nicotine Dependence, Sustained Full Remission; Nicotine Dependence, Sustained Partial Remission; Nicotine Dependence, On Agonist Therapy; Opioid Withdrawal; Opioid-Related Disorder Not Otherwise Specified; Opioid Dependence, with physiological dependence; Opioid Dependence, without physiological dependence; Opioid Dependence, Early Full Remission; Opioid Dependence, Early Partial Remission; Opioid Dependence, Sustained Full Remission; Opioid Dependence, Sustained Partial Remission; Opioid Dependence On Agonist Therapy; and Opioid Dependence in a controlled environment; Ethanol Withdrawal; Ethanol Dependence with Physiological Dependence; Ethanol Withdrawal, without Physiological Dependence; Ethanol Withdrawal, Early Full Remission; Ethanol Withdrawal, Early Partial Remission; Ethanol Withdrawal, Sustained Full Remission; Ethanol Withdrawal, Sustained Partial Remission; Ethanol Withdrawal, on Agonist Therapy; and Ethanol Withdrawal, In a Controlled Environment.

The discontinued use of tobacco products, all of which contain nicotine, results in the onset of nicotine withdrawal conditions. Individuals typically suffer the symptoms of nicotine withdrawal as a consequence of the discontinued use of tobacco in any form, including, but not limited to smoking of cigarette, cigar, or pipe tobacco, or the oral or intranasal ingestion of tobacco or chewing tobacco. Such oral or intranasal tobacco includes, but is not limited to snuff and chewing tobacco. The cessation of nicotine use or reduction in the amount of nicotine use, is often followed within 24 hours by symptoms including dysphoric, depressed mood; light-headedness; insomnia; irritability, frustration or anger; anxiety; nervous tremor; difficulty concentrating; restlessness; decreased heart rate; increased appetite or weight gain; and the craving for tobacco or nicotine. These symptoms often cause clinically significant distress or impairment in social, occupational, or other important areas of functioning. The present invention is most preferably used to alleviate one or more symptoms attributed to nicotine withdrawal when such symptoms are not due to a general medical condition and are not better accounted for by another medical disorder.

The present method is also helpful to those who have replaced, or partially replaced, their use of tobacco with the use of nicotine replacement therapy. Thus, such patients can be assisted to reduce and even eliminate entirely their dependence on nicotine in all forms.

The discontinued or reduction in administration of an opioid, typically self-administration, through injection or orally, through smoking or intranasal ingestion, results in the presence of a characteristic opioid withdrawal condition. This withdrawal condition is also precipitated by administration of an opioid antagonist such as naloxone or naltrexone after opioid use. Opioid withdrawal is characterized by symptoms that are generally opposite to the opioid agonist effects. These withdrawal symptoms include anxiety; restlessness; muscle aches, often in the back and legs; craving for opioids; irritability and increased sensitivity to pain; dysphoric mood; nausea or vomiting; lacrimation; rhinorrhoea; papillary dilation; piloerection; sweating; diarrhea; yawning; fever; and insomnia. When dependence is on short-acting opioids, such as heroin, withdrawal symptoms occur within 6–24 hours after the last dose, while with longer-acting opioids, such as methadone, symptoms may take 2–4 days to emerge. These symptoms often cause clinically significant distress or impairment in social, occupational or other important areas of functioning. The present invention is most preferably used to alleviate one or more symptoms attributed to opioid withdrawal when such symptoms are not due to a general medical condition and are not better accounted for by another medical disorder.

The discontinued or reduction in use of ethanol (ethanol containing beverages) results in the onset of ethanol withdrawal conditions. Ethanol withdrawal conditions are characterized by symptoms that begin when blood concentrations of ethanol decline sharply, within 4 to 12 hours after ethanol use has been stopped or reduced. These ethanol withdrawal symptoms include craving for ethanol; autonomic hyperactivity (such as sweating or pulse rate greater than 100); hand tremor; insomnia; nausea; vomiting; transient visual, tactile, or auditory hallucinations or illusions; psychomotor agitation; anxiety; and grand mal seizures. These symptoms often cause clinically significant distress or impairment in social, occupational, or other important areas of functioning. The present invention is most preferably used to alleviate one or more symptoms attributed to ethanol withdrawal when such symptoms are not due to a general medical condition and are not better accounted for by another medical disorder.

The method of the present invention is preferably administered in connection with and/or subsequent to an educational and/or behavioral modification program to enhance continued abstinence from tobacco, opioids, ethanol, or combinations thereof. The method of the present invention is also highly beneficial to such programs by alleviating the suffering experienced from the nicotine, opioid, and ethanol withdrawal over the course of such programs. Therefore, the programs can be more effective by focusing on educational and behavioral modification goals, further reducing the incidence of program non-completion.

The compound 4-chloro-5--(imidazoline-2-ylamino)-6-methoxy-2-methylpyrimidine is prepared generally as disclosed in U.S. Pat. No. 4,323,570. Preferably, 4-chloro-5-(imidazoline-2-ylamino)-6-methoxy-2-methylpyrimidine is prepared as follows.

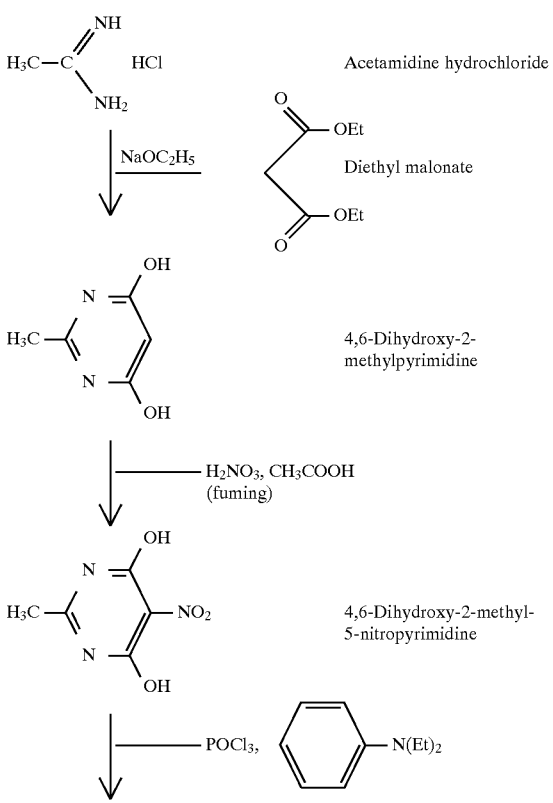

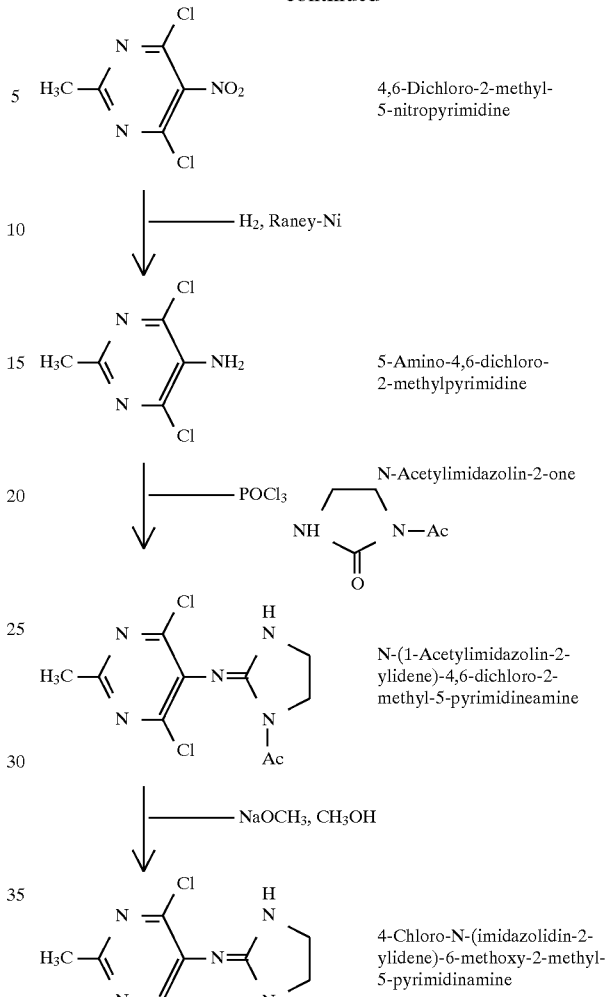

N-acetelimidazoline-2-one is prepared by reacting acetic anhydride with 2-imidazolidone at room temperature. The reaction mixture is heated to between 80° C. and 100° C. for 90 minutes and then cooled to from about 10° C. to about −10° C. to afford N-acetelimidazoline-2-one.

The first intermediate, 4,6-dihydroxy-2-methylpyrimidinamine, is synthesized by preparing sodium ethoxide in situ from sodium and an hydrous ethanol under a nitrogen blanket. Acetamidine hydrochloride and diethyl malonate are added and the reaction mixture heated to boiling for 2 to 5 hours to afford 4,6-dihydroxy-2-methylpyrimidine.

The second intermediate, 4,6-dihydroxy-2-methyl-5-nitropyrimidine, is then synthesized by slowly adding 4,6-dihydroxy-2-methylpyrimidine to a reaction mixture of fuming nitric acid in acetic acid. Once addition of 4,6-dihydroxy-2-methylpyrimidine is complete, the reaction mixture is stirred for one-half to 2 hours to afford 4,6-dihydroxy-2-methyl-5-nitropyrimidine.

Following the nitration, phosphorous oxychloride (POCl$_3$) and 4,6-dihydroxy-2-methyl-5-nitropyrimidine are combined with stirring. To this mixture, diethylaniline is added dropwise at a rate so that the reaction mixture temperature is maintained below about 40° C. After the addition is complete, the reaction mixture is refluxed for one to three hours and then distilled under a vacuum to afford the third intermediate, 4,6-dichloro-2-methyl-5-nitropyrimidine.

The third intermediate, 4,6-dichloro-2-methyl-5-nitropyrimidine is hydrogenated over Raney-Ni as a 10% to 30% solution in toluene to afford the corresponding compound, 4,6-dichloro-2-methyl-5-aminopyrimidine, as a fourth intermediate.

The fifth intermediate, N-(1-acetylimidazolin-2-ylidene)-4,6-dichloro-5-pyrimidinamine, is then prepared by combining phosphorous oxychloride, N-acetylimidazolin-2-one and 5-amino-4,6-dichloro-2-methylpyrimidine, and heating to boiling during from 2 to 4 hours, and then cooling, with stirring to room temperature.

The final product, 4-chloro-N-(imidazolin-2-ylidene)-6-methoxy-2-methyl-5-pyrimidinamine is synthesized by first preparing sodium methoxide in situ from anhydrous methanol and sodium. The fifth intermediate, N-(1-acetylimidazolin-2-ylidene)-4,6-dichloro-2-methyl-5-pyrimidinamine, is added and the reaction mixture brought to a boil. From 15 minutes to 1 hour after the reaction mixture is brought to a boil, further sodium methoxide is added and the reaction mixture is maintained at a boil for from 15 minutes to 1 hour to afford 4-chloro-N-(imidazolin-2-ylidene)-6-methoxy-2-methyl-5-pyrimidinamine.

Work-up of the several intermediates are carried out by standard techniques well-known to those skilled in the art. The various reactants and reagents used in this synthesis are commercially available or readily prepared from commercially available material by standard methods wellknown to those skilled in the art.

It will be appreciated that the compound of the present invention may be isolated per se or may be converted to an acid addition salt using conventional methods.

By the term "effective dose" is meant an amount of 4-chloro-5-(imidazoline-2-ylamino)-6-methoxy-2-methylpyrimidine, or a pharmaceutically acceptable salt thereof, which will diminish or relieve one or more symptoms or conditions resulting from cessation or withdrawal of tobacco, nicotine, opioids, ethanol and combinations thereof.

The compound of the present invention is an $I_1$-imidazoline ligand demonstrating substantial selectivity for $I_1$ receptors over $\alpha_2$ adrenergic receptors. In saturation binding experiments in bovine rostral ventrolateral medulla (bovine RVLM), moxonidine demonstrates a selectivity value ($K_i$ at $\alpha_2$ sites in uM/$K_i$ at $I_1$ sites in uM) of greater than 20 and preferably greater than 30 x, where $K_i$ is the inhibitory affinity constant. Of course, $K_i$ is inversely proportional to affinity, so lower $K_i$ values indicate higher affinity. Thus, the higher the selectivity value, the more selective the compound. In contrast, clonidine's selectivity value in bovine RVLM is less than 4. See Ernsberger et al., *J. Pharmacol. Exp. Ther.,* 264, 172–182 (1993) for details on experimental protocol and results.

The dose of compound to be administered, in general, is from about 0.001 to about 10.0 mg/day; as usual, the daily dose may be administered in a single bolus, or in divided doses, depending on the judgment of the physician in charge of the case. A more preferred range of doses is from about 0.002 to about 5.0 mg/day; other dosage ranges which may be preferred in certain circumstances are from about 0.005 to about 2.0 mg/day; from about 0.1 to about 1.0 mg/day; from about 0.05 to about 0.8 mg/day; and a particularly preferred range is from about 0.05 to about 0.6 mg/day. It will be understood that the dose for a given patient is always to be set by the judgment of the attending physician, and that the dose is subject to modification based on the size of the patient, the lean or fat nature of the patient, the characteristics of the particular compound chosen, the intensity of the patient's tobacco, opioid, ethanol or combinations thereof habit, the intensity of the patient's withdrawal symptoms, and psychological factors which may affect the patient's physiological responses.

THE FORMULATIONS

Pharmaceuticals are substantially always formulated into pharmaceutical dosage forms, in order to provide an easily controllable dosage of the drug, and to give the patient an elegant and easily handled product. The present compound is susceptible to formulation into the conventional pharmaceutical dosage forms, including capsules, tablets, inhalants, injectable parenteral solutions and suppositories. Usually the oral dosage forms, particularly tablets and capsules, are most convenient for the patient and are usually preferred. Liquid suspensions of pharmaceuticals, formerly popular, have now become less popular and are seldom used but the present compounds are entirely amenable to such products should they be desired.

While it is possible to administer 4-chloro-5-(imidazoline-2-ylamino)-6-methoxy-2-methylpyrimidine directly, it is preferably employed in the form of a pharmaceutical formulation comprising a pharmaceutically acceptable carrier, diluent or excipient and the compound. Such formulations will contain from about 0.01 percent to about 99 percent of the compound.

In making the formulations of the present invention, the active ingredient will usually be mixed with at least one carrier, or diluted by at least one carrier, or enclosed within a carrier which may be in the form of a capsule, sachet, paper or other container using conventional techniques and procedures for the preparing of pharmaceutical formulations. When the carrier serves as a diluent, it may be a solid, semi-solid or liquid material which acts as a vehicle, excipient or medium for the active ingredient. Thus, the formulations can be in the form of tablets, granules, pills, powders, lozenges, sachets, cachets, elixirs, emulsions, solutions, syrups, suspensions, aerosols (as a solid or in a liquid medium) and soft and hard gelatin capsules.

Examples of suitable carriers, diluents and excipients include lactose, dextrose, sucrose, sorbitol, mannitol, starches, gum acacia, calcium phosphate, alginates, liquid paraffin, calcium silicate, microcrystalline cellulose, polyvinylpyrrolidone, cellulose, tragcanth, gelatin, syrup, methylcellulose, methyl- and propylhydroxybenzoates, vegetable oils, such as olive oil, injectable organic esters such as ethyl oleate, talc, magnesium stearate, water and mineral oil. The formulations may also include wetting agents, lubricating, emulsifying and suspending agents, preserving agents, sweetening agents, perfuming agents, stabilizing agents or flavoring agents. The formulations of the invention may be formulated so as to provide immediate or nonimmediate release of the active ingredient, by procedures well-known in the art. Preferably, the formulations of the present invention will be formulated to provide nonimmediate release of the active ingredient for oral or transdermal administration.

In nonimmediate release dosage forms, release of the drug from its dosage form is the rate limiting step in the release-absorption-elimination kinetic scheme. This is distinguished from the immediate release dosage forms where absorption of drug across a biological membrane is a rate limiting step.

Nonimmediate release delivery systems have been divided into four categories: (1) delayed release; (2) sustained release; (3) site-specific release; and (4) receptor release.

Generally, delayed release systems are those that employ repetitive, intermediate dosing of a drug from one or more immediate release units incorporated into a single dosage form. Examples of delayed release systems include repeat action tablets and capsules and enteric-coated tablets where timed release is achieved by a barrier coating.

Sustained release delivery systems include both controlled release and prolonged release. Generally, sustained release systems include any drug delivery system that achieves slow release of drug over an extended period of time. When the system maintains constant drug levels in the blood or target tissue. It is considered a controlled release system. Where the system extends the duration of action over that afforded by a conventional delivery system, it is considered a prolonged release system.

Site-specific and receptor release systems refer to targeting of a drug directly to a desired biological location. In the case of site-specific release, a target is a particular organ or tissue. Analogously, in the case of receptor release, the target is the particular receptor for a drug within a particular organ or tissue.

Typical oral nonimmediate release forms include diffusional systems and dissolution systems. In diffusional systems, the release rate of drug is determined by its diffusion through a water-insoluble polymer. There are generally two types of diffusional devices, reservoir devices in which a core of drug is surrounded by polymeric membrane; and matrix devices in which dissolved or dispersed drug is distributed substantially uniformly and throughout an inert polymeric matrix. In actual practice, many systems that utilize diffusion may also rely to some extent on dissolution to determine the release rate.

Common practices utilized in developing reservoir systems include microencapsulation of drug particles and press-coating of whole tablets or particles. Frequently, particles coated by microencapsulation form a system where the drug is contained in the coating film as well as in the core of the microcapsule. Drug release typically includes a combination of dissolution and diffusion with dissolution being the process that controls the release rate. Common material is used as the membrane barrier coat, alone or in combination, are hardened gelatine, methyl and ethylcellulose, polyhydroxymethacrylate, hydroxypropylcellulose, polyvinylacetate, and various waxes.

In matrix systems, three major types of materials are frequently used in the preparation of the matrix systems which include insoluble plastics, hydrophilic polymers, and fatty compounds. Plastic matrices which have been employed include methyl acrylate-methyl methacrylate, polyvinyl chloride and polyethylene. Hydrophilic polymers include methyl cellulose, hydroxypropylcellulose and sodiumcarboxymethylcellulose. Fatty compounds include various waxes such as carnauba wax, and glyceryl tristearate. Preparation of these matrix systems are by methods well known to those skilled in the art. These methods of preparation generally comprise mixing the drug with the matrix material and compressing the mixture into tablets. With wax matrixes, the drug is generally dispersed in molten wax, which is then congealed, granulated and compressed into cores. As with other nonimmediate systems, it is common for a portion of the drug to be available immediately as a priming dose and the remainder to be released in a sustained fashion. This is generally accomplished in the matrix system by placing a priming dose in a coat on the tablet. The coat can be applied by press coating or by conventional pan or air suspension coating.

Dissolution systems generally are products that have a decreased dissolution rate where the drug is highly soluble. Several approaches to achieving a slow dissolution rate include preparing an appropriate salt or derivative of the active agent, by coating the drug with a slowly dissolving material, or by incorporating the drug into a tablet with a slowly dissolving carrier. Encapsulated dissolution systems are prepared either by coating particles or granules of drug with varying thickness' of slowly soluble polymers or by microencapsulation. The most common method of microencapsulation is coacervation, which involves addition of a hydrophilic substance to a coloidal dispersion. The hydrophilic substance, which operates as the coating material, is selected from a wide variety of natural and synthetic polymers including shellacs, waxes, starches, cellulose acetate, phthalate or butyrate, polyvinylpyrrolidone, and polyvinyl chloride. After the coating material dissolves, the drug inside the microencapsule is immediately available for dissolution and absorption. Drug release, therefore, can be controlled by adjusting the thickness and dissolution rate of the coat. For example, the thickness can be varied from less than one $\mu$m to 200 $\mu$m by changing the amount of coating material from about 3 to about 30 percent by weight of the total weight. By employing different thickness', typically three of four, the active agent will be released at different, predetermined times to afford a delayed release affect. Coated particles can, of course, be directly compressed into tablets or placed into capsules.

Matrix dissolution systems are prepared by compressing the drug with a slowly dissolving polymer carrier into a tablet. Generally there are two methods for preparing drug-polymer particles, congealing and aqueous dispersion methods. In the congealing method, the drug is mixed with a polymer or wax material and either-cooled or cooled and screened or spray-congealed. In the aqueous dispersion method, the drug-polymer mixture is simply sprayed or placed in water and the resulting particles are collected.

Osmotic systems are also available where osmotic pressure is employed as the driving force to afford release of a drug. Such systems generally consist of a core of drug surrounded by a semipermeable membrane containing one or more orifices. The membrane allows diffusion of water into the core, but does not allow release of the drug except through the orifices. Examples of materials used as the semipermeable membrane include polyvinyl alcohol, polyurethane, cellulose acetate, ethylcellulose, and polyvinyl chloride.

A further system comprises ion-exchange resins. These resins are water-insoluble cross-linked polymers containing salt forming groups in repeating positions on the polymer chain. The active agent is bound to the resin by repeated exposure of the resin to the drug in a chromatographic column, or by prolonged contact of the resin with a solution of the drug. Drug release from the drug-resin complex depends on the ionic environment; that is pH and electrolyte concentration within the gastrointestinal tract, as well as the specific properties of the resin. Drug molecules attached to the resin are released by changing with appropriately charged ions in the gastrointestinal tract followed by infusion of the free drug molecule out of the resin. Generally, the rate of diffusion is controlled by the area of diffusion, diffusional path link, and extent of crosslinking in the resin. A further modification of the release rate can be afforded by coating the drug-resin complex.

The most common types of dosage forms used for parenteral nonimmediate release drug therapy are intramuscular injections, implants for subcutaneous tissues and various body cavities, and transdermal devices. Generally, intramuscular injections involve a formation of a dissociable complex of a drug with another molecule. In this sense, the drug-molecule complex serves as a reservoir at the site of injection for drug release to the surrounding tissues. Examples of macromolecules include biological polymers such as antibodies and proteins or synthetic polymers such as polyvinylpyrrolidone, and polyethylene glycol.

Complexes can also be formed between drugs and small molecules. When the drug molecule is large relative to the complexing agent, the association constant will be greater and the complex more stable. Examples for smaller molecules include zinc, optionally suspended in a gelatin solution or an oil solution. An alternative dosage form for an intramuscular injection is an aqueous suspension. By varying viscosity and particle size a stable suspension of active ingredient can be afforded. Another common approach to decreased dissolution rate is to decease the saturation solubility of the drug. This is accomplished through the formation of less soluble salts and prodrug derivatives and by employing polymorphic crystal forms of the active ingredient.

Another approach is a use of oil solutions and oil suspensions. As will be appreciated by those skilled in the art, those drugs having appreciable oil solubility and the desired partition characteristics are most suitable for this approach. Examples of oils which may be used for intramuscular injection include sesame, olive, arachnis, maize, almond, cotton seed and caster oil. With oil suspensions, drug particles must first dissolve in the oil phase and then partition into the aqueous medium.

Emulsions comprising oil-in-water emulsions or water-in-oil emulsions may also be used.

Implants comprise a drug-barring polymeric device which is inserted subcutaneously or in various body cavities. The polymer material which is used must, of course, be biocompatible and nontoxic and are typically chosen from among hydrogels, silicones, polyethylenes, ethylene-vinyl acetate copolymers, and biodegradable polymers. Hydrogels generally are a polymeric material that exhibit the ability to swell in water and retain greater than 20 percent of that water within its structure, but which will not dissolve in water. Small molecular weight substances are capable of diffusing through hydrogels. Specific example of hydrogels include polyhydroxyalkyl methacrylates, polyacrylamide and polymethacrylamide, polyvinylpyrrolidone, polyvinyl alcohol, and various polyelectrolyte complexes.

Additional systems include subcutaneous devices, and intravaginal devices.

Percutaneous drug absorption, more commonly referred to as transdermal systems, generally includes the use of microporous membranes as the rate controlling barrier. Microporous membranes are films varying in thickness with pore sizes ranging from several micrometers to a few angstroms. Examples of material from which such membranes are made include regenerated cellulose, cellulose nitrates/acetate, cellulose triacetate, polypropylene, polycarbonate and polytetrafluoroethylene. The barrier properties of these various films depend upon the method of preparation, the medium with which the pores are filled, pore diameter, percent porosity, and tortuosity.

An example of a transdermal system is disclosed in U.S. Pat. No. 4,201,211.

Targeted delivery systems include nanoparticles and liposomes. Nanoparticles are examples of systems known collectively as colloidal drug delivery systems. Other members in this group include microcapsules, nanocapsules, macromolecular complexes, polymeric beads, microspheres and liposomes. Generally, a nanoparticle is a particle containing dispersed drug with a diameter of 200–500 nm. Materials used in the preparation of nanoparticles are sterilisable, nontoxic and biodegradable. Examples include albumen, ethylcellulose, casein and gelatin. Typically, they are prepared by procedures similar to the coacervation method of microencapsulation.

Liposomes, generally, are phospholipids that when dispersed with aqueous media swell, hydrate and form multilamellar concentric bilayer vesicles with layers of aqueous media separating the lipid bilayers. Phospholipids can also form a variety of structures other than liposomes when dispersed in water depending on the molar ration of lipid to water. At low ratios, the liposome is the preferred structure. The actual physical characteristics of the liposomes depend on pH, ionic strength and the presence of divalent cations. They show low permeability to ionic and polar substances but at elevated temperatures undergo a phase transition which alters their permeability. Polar drugs are trapped in the aqueous spaces and nonpolar drugs bind to the lipid bilayer of vesicle. Polar drugs are released when the bilayer is broken or by permeation, but nonpolar drugs remain affiliated with the bilayer until it is disrupted by temperature or exposure to lipoproteins. The liposome, of course, acts as the carrier or the active agent.

Depending on the method of administration, the formulations for the treatment of the nicotine withdrawal, opioid withdrawal, ethanol withdrawal and combinations thereof, conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.01 to 0.4 mg, more usually 0.05 to 0.3 mg, of the active ingredient. The term "unit dosage form" refers to physically discrete units suitable as unitary dosages for human subjects and other mammals, each unit containing a predetermined quantity of active material calculated to produce the desired therapeutic effect, related to the desired daily or divided dose, in association with a suitable pharmaceutical carrier, diluent or excipient therefor. When a sustained release formulation is desired, the unit dosage form may contain from 0.01 to 2.0 mg of the active ingredient. A preferred formulation of the invention is a nonimmediate release or transdermal patch comprising 0.01 to 2.0 mg or 0.05 to 2.0 mg of active ingredient together with a pharmaceutically acceptable carrier therefor.

In order to more fully illustrate the operation of this invention, the following examples of formulations are provided. The examples are illustrative only and are not intended to limit the scope of the invention.

FORMULATION 1
Hard gelatin capsules are prepared using the following ingredients:

| | Amt. per Capsule | Concentration by Weight (percent) |
|---|---|---|
| 4-chloro-5-(imidazoline-2-ylamino)-6-methoxy-2- | 10 mg | 4.2 |

-continued

| | | |
|---|---|---|
| methylpyrimidine | | |
| Starch dried | 220 mg | 91.7 |
| Magnesium stearate | 10 mg | 4.2 |
| | 240 mg | 101.1 |

The above ingredients are mixed and filled into hard gelatin capsules in 240 mg quantities.

FORMULATION 2
Capsules each containing 10 mg of medicament are made as follows:

| | Amt. per Capsule | Concentration by Weight (percent) |
|---|---|---|
| 4-chloro-5-(imidazoline-2-ylamino)-6-methoxy-2-methylpyrimidine | 10 mg | 5.3 |
| Starch dried | 89 mg | 46.8 |
| Microcrystalline cellulose | 89 mg | 46.8 |
| Magnesium stearate | 2 mg | 1.1 |
| | 190 mg | 100.0 |

The active ingredient, cellulose, starch and magnesium stearate are blended, passed through a No. 45 mesh U.S. sieve and filled into a hard gelatin capsule.

FORMULATION 3
Capsules each containing 10 mg of active ingredient are made as follows:

| | Amt. per Capsule | Concentration by Weight (percent) |
|---|---|---|
| 4-chloro-5-(imidazoline-2-ylamino)-6-methoxy-2-methylpyrimidine | 10 mg | 3.2 |
| Polyoxyethylenesorbitan | 50 mg | 16.1 |
| Magnesium stearate | 250 mg | 80.6 |
| | 310 mg | 99.9 |

The above ingredients are thoroughly mixed and placed in an empty gelatin capsule.

FORMULATION 4
Tablets each containing 10 mg of active ingredient are made up as follows:

| | Amt. per Capsule | Concentration by Weight (percent) |
|---|---|---|
| 4-chloro-5-(imidazoline-2-ylamino)-6-methoxy-2-methylpyrimidine | 10 mg | 10.0 |
| Starch | 45 mg | 45.0 |
| Microcrystalline cellulose | 35 mg | 35.0 |
| Polyvinyl (pyrrolidone (as 10% solution in water) | 4 mg | 4.0 |
| Sodium carboxyethyl starch | 4.5 mg | 4.5 |
| Magnesium stearate | 0.5 mg | 0.5 |
| Talc | 1 mg | 1.0 |
| | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through No. 18 mesh U.S. sieve. The sodium carboxymethyl starch, magnesium stearate and talc, previously passed though a No. 60 mesh U.S. sieve, are then added to the granule which, after mixing, is compressed on a tablet machine to yield a tablet weighing 100 mg.

FORMULATION 5
A tablet formula may be prepared using the ingredients below:

| | Amt. per Capsule | Concentration by weight (percent) |
|---|---|---|
| 4-chloro-5-(imidazoline-2-ylamino)-6-methoxy-2-methylpyrimidine | 5 mg | 1.2 |
| Cellulose microcrystalline | 400 mg | 95.2 |
| Silicon dioxide fumed | 10 mg | 2.4 |
| Stearic acid | 5 mg | 1.2 |
| | 420 mg | 100.0 |

The components are blended and compressed to form tablets each weighing 420 mg.

FORMULATION 6
Suspensions each containing 5 mg of medicament per 40 ml dose are made as follows:

| | Per 5 ml of suspension |
|---|---|
| 4-chloro-5-(imidazoline-2-ylamino)-6-methoxy-2-methylpyrimidine | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

THE TESTING METHODS

The usefulness of the compound for treating a condition resulting from cessation and withdrawal from the use of nicotine and lack of sedating effect was supported by the following studies.

I. Auditory Startle Response.

Animals:

Male Long Evans rats (Harlan Sprague Dawley, Columbus, Indiana) are individually housed in a controlled environment on a 12 hour light-dark cycle. The rats are given free access to food (Purina Rodent Chow) and water. All treatment groups contain from 8 to 10 rats.

Chronic Nicotine Treatment

The rats are anesthetized with isoflurane and Alzet osmotic minipumps (Alza Corporation, Palo Alto, California Model 2ML2) are implanted subcutaneously. Nicotine ditartrate is dissolved in physiological saline. Pumps are filled with nicotine ditartrate (6 mg/kg base/day) or physiological saline. Twelve days following implantation of pumps, rats are anesthetized with isoflurane and the pumps are removed.

Auditory Startle Response Observation

The sensory motor reactions [auditory startle response (peak amplitude, $V_{max}$)] of individual rats are recorded using San Diego Instruments startle chambers (San Diego, California). Startle sessions consist of a 5 minute adaptation period at background noise level of 70+/−2dBA immediately followed by 25 presentations of auditory stimuli (120+/−2 dBA noise, 50 ms duration) presented at 8 second intervals.

Peak startle amplitudes are averaged for all 25 presentations of stimuli for each session. Auditory startle responding is evaluated daily at 24 hour intervals on days 1, 2, and 3 following nicotine withdrawal.

The 4-chloro-5-(imidazoline-2-ylamino)-6-methoxy-2-methylpyrimidine compound is administered subcutaneously at three doses about 15 minutes before startle testing each day. Clonidine was also tested.

Ambulatory Activity Evaluation Spontaneous activity of male Long Evans rats was recorded using Multi-Varimax Activity Monitors (Columbus Instruments, Columbus, Ohio). Interruptions of three individual infrared photocells were recorded by computer. Activity counts were accumulated at 15 minute intervals for 1 hour immediately following administration of 4-chloro-5-(imidazoline-2-ylamino)-6-methoxy-2-methylpyrimidine (0.01, 0.1, 1 mg/kg, s.c.), clonidine (0.1, 0.3, 1.0 mg/kg, s.c.), or the saline control. Ambulatory activity counts represent the sum of individual photocell beam breaks within a representative time interval.

Results: As illustrated in Tables 1, 2, 3 and 4 subcutaneous administration of 4-chloro-5-(imidazoline-2-ylamino)-6-methoxy-2-methylpyrimidine (Moxonidine) 15 minutes prior to startle testing significantly attenuated the effects of nicotine withdrawal of the auditory startle reflex.

The compounds were as follows:

A. Moxonidine

B. Clonidine

TABLE 1

| Chronic Treatment | Pre-Treatment | Startle Response ($\mu V$) | | |
|---|---|---|---|---|
| | | Day 1 | Day 2 | Day 3 |
| Saline | Saline | 229* | 258* | 248* |
| Nicotine | Saline | 368 | 356 | 382 |
| Nicotine | Compound A 0.00003 mg/kg | 406 | 379 | 377 |
| Nicotine | Compound A 0.0001 mg/kg | 271* | 269* | 278* |
| Nicotine | Compound A 0.0003 mg/kg | 237* | 247* | 220* |
| Nicotine | Compound B 0.001 mg/kg | 189* | 233* | 209* |

*Significantly different from Nicotine/Saline control, $P < 0.05$

TABLE 2

| Chronic Treatment | Pre-Treatment | Startle Response ($\mu V$) | |
|---|---|---|---|
| | | Day 1 | Day 2 |
| Saline | Saline | 201 | 236 |
| Nicotine | Saline | 298* | 302* |
| Nicotine | Compound B 0.0001 mg/kg | 288* | 325* |
| Nicotine | Compound B 0.0003 mg/kg | 231 | 317* |
| Nicotine | Compound B 0.001 mg/kg | 196 | 256 |

*Significantly different from Saline/Saline control, $P < 0.05$

TABLE 3

Acute Effect

| Pre-Treatment | Startle Response ($\mu V$) Day 1 |
|---|---|
| Saline | 211 |
| Compound A 0.001 mg/kg | 230 |
| Compound A 0.01 mg/kg | 213 |
| Compound A 0.1 mg/kg | 203 |
| Compound A 1.0 mg/kg | 105* |

*Significantly different from Saline control, $P < 0.05$

TABLE 4

Acute Effect

| Pre-Treatment | Startle Response ($\mu V$) Day 1 |
|---|---|
| Saline | 182 |
| Compound B 0.003 mg/kg | 168 |
| Compound B 0.01 mg/kg | 148 |
| Compound B 0.03 mg/kg | 135* |
| Compound B 0.1 mg/kg | 126* |
| Compound B 0.3 mg/kg | 50* |

*Significantly different from Saline control, $P < 0.05$

TABLE 5

Spontaneous Activity Levels (Counts)

| Treatment | Time (minutes) | | | |
|---|---|---|---|---|
| | 15 | 30 | 45 | 60 |
| Vehicle | 82 | 48 | 46 | 31 |
| Compound A 0.01 mg/kg | 95 | 52 | 44 | 36 |
| Compound A 0.1 mg/kg | 75 | 38 | 31 | 21 |
| Compound A 1.0 mg/kg | 65 | 19* | 4* | 7 |
| Compound B 0.03 mg/kg | 33* | 16* | 14* | 15 |

*Significantly different from Vehicle control, $P < 0.05$.

Conclusion

As can be seen in Table 2 above, subcutaneously administered clonidine does effectively reduce the elevation in startle reactivity typically observed in rats experiencing nicotine withdrawal. The $ED_{50}$ for subcutaneously administered clonidine in this model is approximately 0.0004 mg/kg.

Treatment with moxonidine prior to startle testing during nicotine withdrawal also effectively blocks the hyperreactivity that is typically seen ($ED_{50}$ approximately 0.00007 mg/kg; see Table 1, above). These data indicate that moxonidine may be a useful as an aid to smoking cessation and nicotine withdrawal in mammals at a significant and unexpected lower doses than clonidine.

Since the effects observed on auditory startle might be partially produced by drug related sedation or the inability to respond on the startle task, rats were also evaluated to determine the comparative effects of moxonidine and clonidine on locomotor activity and startle responding in non-nicotine dependent animals.

The results of activity testing for clonidine and moxonidine are presented above in Table 5. As can be seen, clonidine significantly reduced ambulatory activity at doses ≧0.03 mg/kg. Moxonidine also reduced ambulatory activity but a dose of 1 mg/kg was required to produce a reduction in ambulatory activity similar to the reduction seen with a 0.03 mg/kg dose of clonidine.

Both compounds also reduce auditory startle responding (see Tables 3 and 4) at doses that are equivalent to the doses which reduce ambulation. Again, clonidine is more potent than moxonidine in reducing baseline startle responding.

These data indicate that clonidine produces sedation and interferes with responding at more than 30-fold lower doses than moxonidine.

TABLE 6

Comparison of Moxonidine and Clonidine

| Assay | Moxonidine (mg/kg) | Clonidine (mg/kg) |
|---|---|---|
| Nicotine Withdrawal (ED50) | 0.00007 | 0.0004 |
| Baseline Startle (MED) | 1.0 | 0.03 |
| Locomotor activity (MED) | 1.0 | 0.03 |

Clonidine is able to reduce the nicotine withdrawal-enhanced acoustic startle reflex. However, clonidine also produces sedating side effects at doses that are less than 100-fold higher than the $ED_{50}$ in the nicotine withdrawal assay. This poor separation between efficacy and side effects for clonidine in the rat is expected to parallel its narrow therapeutic window in the treatment of smoking cessation and nicotine withdrawal in man. Moxonidine is more potent than clonidine in the nicotine withdrawal assay and produces sedating side effects only at doses that are greater than 10,000-fold higher than the $ED_{50}$ in the nicotine withdrawal assay. Therefore, moxonidine will have good efficacy as an aid to smoking cessation and nicotine withdrawal without producing the side effects observed with clonidine.

The usefulness of the compound for treating a condition resulting from cessation and withdrawal from opioid use was supported by the following studies.

Materials
Opioid Dependence and Withdrawal

Opioid dependence was induced in male Sprague-Dawley rats (Charles River, 250–350 g) by the s.c. implantation of morphine pellets. Under halothane anesthesia animals were implanted with two pellets (75 mg of morphine/pellet) daily for two days. Withdrawal was induced 48 hours after the last set of pellets was implanted; all four pellets were removed one hour before precipitating withdrawal. Withdrawal was induced by administering the opioid antagonist naltrexone HCl (10 mg/kg; Sigma) s.c.

Behavioral Ratinas

For the behavioral assessment of opioid withdrawal animals were studied in clear plexiglass cages (18×10×8 inches) and remained in these cages for the entire study. Animals were adapted to the cages for 15 minutes and were then administered a pretreatment of either moxonidine or saline (1 ml/kg s.c.). Naltrexone was administered 15 minutes after the pretreatment. Eleven previously identified behaviors characteristic of the rat opioid abstinence syndrome were assessed (see Himmelsback et al, 1935; Way et al., 1969; Wei, 1973; Bläsig et al., 1973; Aceto et al., 1986). The absolute frequency of seven episodic behaviors was recorded and a score was calculated based on multiples of five incidents (0=no incidents; 1=1–5 incidents, etc.). Behaviors scored in this manner included: teeth chatter (separated by at least 3s), jumping, wet-dog shakes, writhing, diarrhea, digging and erections. Chewing (without any matter in the mouth) was similarly scored in multiples of 100 occurrences. Three withdrawal behaviors could not be defined in discrete episodes and the severity of these behaviors was assessed during predefined anchor points on a four point scale: 0=absent; 1=mild; 2=moderate; 3=marked. Behaviors rated in this fashion were lacrimation, ptosis, and salivation. The amount of weight loss was measured at the end of the rating period (i.e. 1 hour after the administration of naltrexone) and a score was calculated based on multiples of 5 g (0=no loss; 1=1–5 g; 2=6–10 g; 3=11–15 g, etc.)

TABLE 7

| Time post Naltrexone (min) | Pretreatment | | |
|---|---|---|---|
| | Saline | Moxonidine 1 mg/kg | Moxonidine 10 mg/kg |
| −15 to 0 | 1.5 | 2 | 1.5 |
| 0 to 15 | 15.25 | 12.5 | 11.5 |
| 15 to 30 | 17.125 | 12 | 10.5* |
| 30 to 45 | 18.125 | 13 | 7.5* |
| 45 to 60 | 16.25 | 11 | 3* |

*Significantly different from saline control, $P < 0.05$.

We claim:

1. A method for treating a condition resulting from the cessation or withdrawal of opioids comprising administering to a mammal in need of such treatment, an effective dose of 4-chloro-5-(imidazoline-2-ylamino)-6-methoxy-2-methylpyrimidine, or a pharmaceutically acceptable salt thereof.

2. A method of claim 1 wherein said condition results from parenteral opioid use.

3. A method of claim 1 wherein said condition results from oral opioid use.

4. A method of claim 1 wherein the condition is Opioid Withdrawal; Opioid Dependence, with physiological dependence; Opioid Dependence, without physiological dependence; Opioid Dependence, Early Full Remission; Opioid Dependence, Early Partial Remission; Opioid Dependence, Sustained Full Remission; Opioid Dependence, Sustained Partial Remission; or Opioid Dependence, On Agonist Therapy.

5. A method of claim 4 wherein the condition is Opioid Withdrawal.

6. A method of claim 1 wherein the effective dose is from about 0.001 mg to about 10.0 mg per day.

7. A method for inhibiting one or more symptoms from the cessation or withdrawal of opioids comprising administering to a mammal in need of such treatment, an effective dose of 4-chloro-5-(imidazoline-2-ylamino)-6-methoxy-2-methylpyrimidine, or a pharmaceutically acceptable salt thereof.

8. A method of claim 7 wherein said symptom is selected from the group consisting of dysphoric mood; nausea; vomiting; muscle aches; lacrimation; rhinorrhoea; papillary dilation; piloerection; sweating; diarrhea; yawning; fever; insomnia; and opioid craving.

9. A method of claim 7 wherein the effective dose is from about 0.001 mg to about 10.0 mg per day.

* * * * *